United States Patent
Cecchi et al.

(10) Patent No.: US 10,722,509 B2
(45) Date of Patent: Jul. 28, 2020

(54) PREDICTING OPTIMAL CHEMOTHERAPY FOR CRC

(71) Applicant: NantOmics, LLC, Culver City, CA (US)

(72) Inventors: Fabiola Cecchi, Washington, DC (US); Todd Hembrough, Gaithersburg, MD (US)

(73) Assignee: NantOmics, LLC, Culver City, CA (US)

( * ) Notice: Subject to any disclaimer, the term of this patent is extended or adjusted under 35 U.S.C. 154(b) by 0 days.

(21) Appl. No.: 16/248,338

(22) Filed: Jan. 15, 2019

(65) Prior Publication Data

US 2019/0216795 A1    Jul. 18, 2019

Related U.S. Application Data

(60) Provisional application No. 62/617,834, filed on Jan. 16, 2018.

(51) Int. Cl.

| | |
|---|---|
| *A61K 31/4745* | (2006.01) |
| *G01N 33/574* | (2006.01) |
| *A61P 35/00* | (2006.01) |
| *A61K 31/282* | (2006.01) |
| *A61K 31/505* | (2006.01) |
| *A61K 38/17* | (2006.01) |
| *G01N 1/30* | (2006.01) |
| *G01N 33/68* | (2006.01) |

(52) U.S. Cl.
CPC ........ *A61K 31/4745* (2013.01); *A61K 31/282* (2013.01); *A61K 31/505* (2013.01); *A61K 38/17* (2013.01); *A61P 35/00* (2018.01); *G01N 1/30* (2013.01); *G01N 33/57419* (2013.01); *G01N 33/6848* (2013.01); *C12Y 304/21004* (2013.01); *G01N 2800/52* (2013.01)

(58) Field of Classification Search
CPC .............. A61K 31/282; A61K 31/4745; A61K 31/505; A61K 38/17; A61P 35/00; C12Y 304/21004; G01N 1/30; G01N 2800/52; G01N 33/57419; G01N 33/6848
See application file for complete search history.

(56) References Cited

U.S. PATENT DOCUMENTS

| | | | |
|---|---|---|---|
| 7,473,532 B2 * | 1/2009 | Darfler | C12N 15/1003 435/7.2 |
| 2019/0262369 A1 * | 8/2019 | Hembrough | A61P 35/00 |

FOREIGN PATENT DOCUMENTS

WO    2016046640 A2    3/2016

OTHER PUBLICATIONS

Teufel et al. Irinotecan plus folinic acid/continous 5-fluorouracil as simplified bimonthly FOLFIRI regimen for first line therapy of metastatic colon cancer. BMC Cancer, 2004, vol. 4, No. 38, pp. 1-8. (Year: 2004).*
Extended European Search Report from European Application No. 19152035.2 dated May 16, 2019.
Yan et al., "Selecting patients with stage II/III colorectal cancer for 5-fluorouracil-based adjuvant chemotherapy using proteomic analysis," Journal of Clinical Oncology, 36(4): supp. 708, Jan. 18, 2018.
Mohelnikova-Duchonova et al., "FOLFOX/FOLFIRI pharmacogenetics: The call for a personalized approach in colorectal cancer therapy," World Journal of Gastroenterology, 20(30): 10316-10330, 2014.

* cited by examiner

*Primary Examiner* — Marcela M Cordero Garcia
(74) *Attorney, Agent, or Firm* — Harness Dickey & Pierce P.L.C.

(57) ABSTRACT

Methods are provided herein for identifying whether a cancer patient, for example a colorectal cancer patient, will be responsive to treatment with a therapeutic strategy comprising administration of the FOLFOX regimen (5-fluorouracil, leucovorin, and oxaliplatin). Specified TYMP and UCK2 fragment peptides are precisely detected and quantitated by SRM-mass spectrometry directly in tumor cells, for example colorectal cancer tumor cells, that are collected from tumor tissue obtained from a cancer patient and compared to reference levels in order to determine if the cancer patients will positively respond to treatment with the combination treatment of FOLFOX (5-fluorouracil, leucovorin, and oxaliplatin).

20 Claims, 3 Drawing Sheets

Specification includes a Sequence Listing.

PREDICTING OPTIMAL CHEMOTHERAPY FOR CRC

CROSS-REFERENCED APPLICATIONS

This application claims the benefit of U.S. Provisional Application No. 62/617,834 filed on 16 Jan. 2018, the entire contents of which are hereby incorporated by reference.

FIELD

Methods are provided for treating cancer patients, for example colorectal cancer (CRC) patients, by assaying tumor tissue surgically-removed from patients and identifying those patients most likely to respond to treatment with the standard chemotherapy strategy comprising administration of the FOLFOX regimen. The FOLFOX regimen comprises treating the cancer patient with a combination of the chemotherapy drugs 5-fluorouracil, leucovorin, and oxaliplatin.

BACKGROUND

Fluorouracil (5-FU), also known as adrucil, is a chemotherapy agent that functions by blocking the production of DNA, which inhibits cell division and thereby prevents tumor cells from dividing and growing. 5-FU acts in several ways, but principally as a thymidylate synthase (TS) inhibitor. Interrupting the action of this enzyme blocks synthesis of the pyrimidine thymidine, which is a nucleoside required for DNA replication. TS methylates deoxyuridine monophosphate (dUMP) to form thymidine monophosphate (dTMP). Administration of 5-FU causes a scarcity in dTM. Thus, rapidly dividing cancerous cells undergo cell death due to lack of thymine. High levels of TS can overcome the effects of 5-FU while high levels of the TYMP protein promotes the activity of 5-FU.

Leucovorin calcium (LV), also known as folinic acid, potentiates the growth inhibitory effects of 5-FU. LV is a precursor for 5,10-methylene-tetrahydrofolate (CH2-THF) and CH2-THF enhances the inhibition of TS by the 5-FU metabolite FdUMP.

Oxaliplatin, also known as eloxatin, is a cancer chemotherapy agent that interferes with DNA replication, thus preventing cells from dividing and leading to tumor cell death via apoptosis. Oxaliplatin is thought to form platinum-DNA adducts in tumor cell DNA, that appear to be more effective at blocking DNA replication and are more cytotoxic than adducts formed from cisplatin. The damaged DNA elicits DNA repair mechanisms, which in turn activate apoptosis when repair proves impossible thus killing the tumor cells.

SUMMARY OF THE INVENTION

The improved methods of treatment described herein identify cancer patients, and in particular colorectal cancer patients, most likely to respond to treatment with administration of the FOLFOX regimen by determining specific levels via SRM mass spectrometry of TYMP and UCK2 proteins directly in tumor cells derived from patient tumor tissue.

DETAILED DESCRIPTION OF THE INVENTION

Figure 1A:
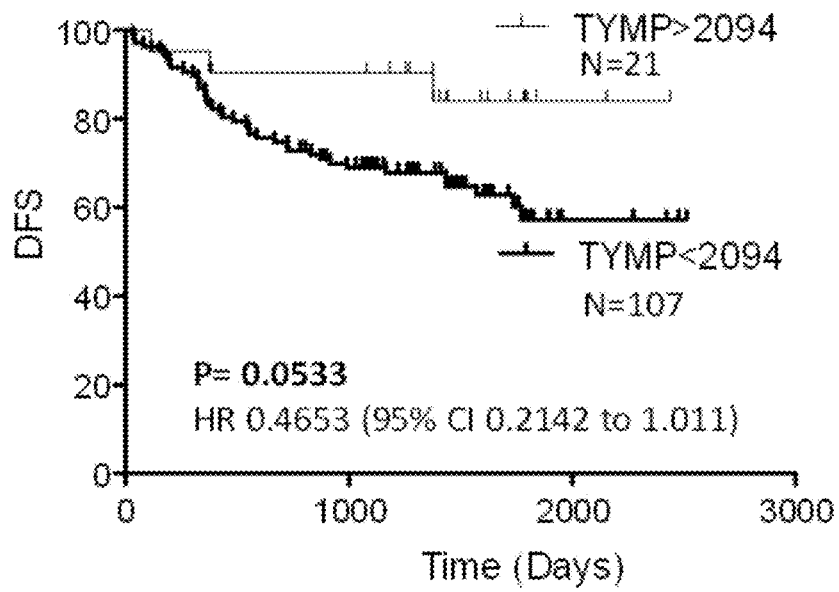
FIGS. 1A and 1B show the Kaplan Meier disease-free survival (DFS) and the overall survival (OS) curves, respectively, using only the TYMP protein levels. Quantitative levels of TYMP at 2094 amol/ug cutoff for this colorectal cancer (CRC) cohort treated with the FOLFOX regimen showed predictive value. Results indicate: a) borderline statistically-significant predictive value for DFS of CRC cancer patients (n=128) based on this TYMP protein level (Mantel-Cox Test p=0.0533; HR 0.4653 (95% CI 0.2142 to 1.011) and b) statistically-significant predictive value for OS of CRC cancer patients (n=128) based on this TYMP protein level (Mantel-Cox Test p=0.0401; HR 0.3667 (95% CI 0.1407 to 0.9559).

Improved methods are provided herein for treating a cancer patient, and particularly a colorectal cancer patient. The treatment methods include determining whether or not the patient will clinically respond in a favorable manner to the therapeutic strategy comprising a first administration of the FOLFOX regimen (fluorouracil, leucovorin, and oxaliplatin). Once this determination is made the patient can be treated with a regimen including FOLFOX or with an alternative regimen.

TYMP, also known as thymidine phosphorylase, is a protein that synthesizes dTMP from thymine and is part of the dTMP biosynthesis salvage pathway, which is itself part of pyrimidine metabolism. TYMP promotes angiogenesis in vivo and has been shown to stimulate the growth of a variety of endothelial cells in vitro. TYMP normally has a highly restricted target cell specificity, acting only on endothelial cells. In some cases, however, TYMP can be abnormally highly expressed in tumor cells. TYMP converts 5-dFUR to 5FU and 5FU to FdUMP which inhibits TS protein, blocking the production of DNA and inducing tumor cell apoptosis.

UCK2 (also known as uridine-cytidine kinase 2) is an enzyme that catalyzes the phosphorylation of uridine and cytidine to uridine monophosphate (UMP) and cytidine monophosphate (CMP), respectively. This is the first step in the production of the pyrimidine nucleoside triphosphates required for RNA and DNA synthesis. UCK2 has been shown to be an integral part of the fluoropyrimidine pathway and, when highly expressed in a tumor cell, promotes greater sensitivity to treatment with 5FU. Conversely, lower to no expression of UCK2 helps confer 5FU resistance on tumor cells. The presence and quantitative levels of UCK2 is related to the probability that a tumor cell may be sensitive or resistant to treatment with 5-FU and, accordingly, it would be very informative to the cancer treatment decision process to know the quantitative amount of the UCK2 protein in patient tumor cells.

TYMP and UCK2 are prognostic predictors of therapeutic outcome in cancer patients and as such can provide information about chemotherapy treatment strategies of cancer. The presence and/or quantitative levels of TYMP and UCK2 protein expression in patient tumor cells procured from patient tumor tissue are determined by quantitating a specified peptide derived from subsequences of each of the TYMP and UCK2 full-length proteins using the methodology of SRM mass spectrometry. Specific quantitative levels of the TYMP protein as detected by SRM mass spectrometry in cancer cells present within a cancer patient indicate that the patient is either more or less likely to respond in a positive manner to a chemotherapy regimen containing 5FU. Specific quantitative levels of the UCK2 protein as detected in cancer cells within a cancer patient by SRM mass spectrometry indicate that the patient is more or less likely to respond in a positive manner to a chemotherapy regimen that includes 5FU.

To determine whether or not the patient will clinically respond to a regimen including FOLFOX, diagnostic methods for measuring the TYMP and UCK2 proteins in a tumor sample or samples from the patient are provided. The sample is advantageously formalin-fixed. Using an SRM/MRM assay that can measure both (for example substantially simultaneously) a specific TYMP peptide fragment and a specific UCK2 peptide fragment, and particular characteristics about the peptide fragments, the amount of the TYMP and UCK2 proteins in cells derived from formalin-fixed paraffin embedded (FFPE) tissue is determined. The peptide fragments derive from the full-length TYMP and UCK2 proteins, wherein the peptide sequence for TYMP protein is SEQ ID NO:1 (DGPALSGPQSR) while the peptide sequence for UCK2 protein is SEQ ID NO:2 (LFVDT-DADTR). Surprisingly it has been found that these peptides can be reliably detected and quantitated simultaneously in protein digests prepared from FFPE samples of tumor tissue. The TYMP peptide is unique to the TYMP protein and the UCK2 peptide is unique to the UCK2 protein: accordingly, one mole of protein will produce one mole of peptide and measurement of the amount of peptide is a direct measurement of the amount of the corresponding protein.

More specifically, these SRM/MRM assays can measure these peptides directly in complex protein lysate samples prepared from cells procured from patient tissue samples, such as formalin-fixed cancer patient tissue. The most widely and advantageously available form of tissue, and cancer tissue, from cancer patients is formalin-fixed, paraffin embedded tissue. Formaldehyde/formalin fixation of surgically removed tissue is by far the most common method of preserving cancer tissue samples worldwide and is the accepted convention in standard pathology practice. Aqueous solutions of formaldehyde are referred to as formalin. "100%" formalin consists of a saturated solution of formaldehyde (about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long-term storage at room temperature. Thus molecular analytical methods to analyze formalin-fixed cancer tissue will be the most accepted and heavily utilized methods for analysis of cancer patient tissue.

Further, methods of preparing protein samples from formalin-fixed tissue, such as FFPE tissue, are described in U.S. Pat. No. 7,473,532, the contents of which are hereby incorporated by reference in their entirety. The methods described in U.S. Pat. No. 7,473,532 may conveniently be carried out using Liquid Tissue® reagents and protocol available from Expression Pathology Inc. (Rockville, Md.). For example, a composition comprising the formalin-fixed tumor sample and a reaction buffer can be heated at a temperature from 80° C. to 100° C. for a period of time from 10 minutes to 4 hours. Additionally, the resulting composition with an effective amount of a proteolytic enzyme selected from the group consisting of trypsin, chymotrypsin, and endoproteinase Lys-C for a period of time from 30 minutes to 24 hours at a temperature from 37° C. to 65° C. In a particular embodiment, the proteolytic enzyme is trypsin.

Results from these SRM/MRM assays can be used to correlate accurate and precise quantitative levels of the TYMP and UCK2 proteins within the specific cancer of the patient from whom the tissue was collected and preserved, including gastric cancer tissue. This not only provides diagnostic/prognostic information about the cancer, but also permits a physician or other medical professional to determine appropriate therapy for the patient. In this case, utilizing these assays provides information about specific levels of TYMP and UCK2 protein expression together or simultaneously in cancer tissue and allows a determination of whether or not the patient from whom the cancer tissue was obtained will respond in a favorable way to the therapeutic strategy comprising administering the FOLFOX regimen (5-fluorouracil, leucovorin, and oxaliplatin).

Treating cancer patients with the FOLFOX regimen is a common and effective strategy for treating cancer and prolonging the lives of cancer patients, especially gastric cancer patients. As explained above, higher levels of the TYMP protein are desirable when treating a cancer patient with the FOLFOX regimen that includes 5FU. It therefore is useful for a clinician to know quantitative levels of the TYMP protein in a patient's cancer cells to allow an informed decision whether or not to treat the patient with a regimen that includes the FOLFOX chemotherapeutic regimen. Similarly, higher levels of the UCK2 protein also are desirable when treating the cancer patient with a regimen that includes 5FU. It therefore is useful for a clinician to know quantitative levels of the UCK2 protein in a patient's cancer cells to allow an informed decision whether or not to treat the patient with a regimen that includes the FOLFOX chemotherapeutic regimen.

Presently the most widely-used and applied methodology to determine protein presence in cancer patient tissue, especially FFPE tissue, is immunohistochemistry (IHC). IHC methodology utilizes an antibody to detect the protein of interest. The results of an IHC test are most often interpreted by a pathologist or histotechnologist. This interpretation is subjective and does not provide quantitative data that are predictive of sensitivity to therapeutic agents that target specific oncoprotein targets, such as 5FU and docetaxel sensitivity in a TYMP and UCK2 positive tumor cell population.

Research from other IHC assays, such as the Her2 IHC test suggest the results obtained from such tests may be wrong. This is probably because different labs have different rules for classifying positive and negative IHC status. Each pathologist running the tests also may use different criteria to decide whether the results are positive or negative. In most cases, this happens when the test results are borderline, meaning that the results are neither strongly positive nor strongly negative. In other cases, tissue from one area of cancer tissue can test positive while tissue from a different area of the cancer tissue tests negative. Inaccurate IHC test results may mean that patients diagnosed with cancer do not receive the best possible care. If all or part of a cancer is positive for a specific target oncoprotein but test results classify it as negative, physicians are unlikely to recommend the correct therapeutic treatment, even though the patient could potentially benefit from those agents. If a cancer is oncoprotein target negative but test results classify it as positive, physicians may recommend a specific therapeutic treatment, even though the patient is unlikely to get any benefits and is exposed to the agent's secondary risks. Accordingly, there is great clinical value in the ability to correctly evaluate quantitative levels of the TYMP and UCK2 proteins in tumors, especially colorectal tumors, so that the patient will have the greatest chance of receiving the most optimal treatment.

Detection of peptides and determining quantitative levels of specified TYMP and UCK2 fragment peptides are determined in a mass spectrometer by the SRM/MRM methodology, whereby the SRM/MRM signature chromatographic peak area of each peptide is determined within a complex peptide mixture present in a Liquid Tissue lysate (see U.S. Pat. No. 7,473,532, as described above). Quantitative levels of the TYMP and UCK2 proteins are then determined by the SRM/MRM methodology whereby the SRM/MRM signature chromatographic peak area of an individual specified peptide from each of the TYMP and UCK2 proteins in one biological sample is compared to the SRM/MRM signature chromatographic peak area of a known amount of a "spiked" internal standard for each of the individual specified TYMP and UCK2 fragment peptides. In one embodiment, the internal standard is a synthetic version of the same exact TYMP and UCK2 fragment peptides where the synthetic peptides contain one or more amino acid residues labeled with one or more heavy isotopes. Such isotope labeled internal standards are synthesized so that mass spectrometry analysis generates a predictable and consistent SRM/MRM signature chromatographic peak that is different and distinct from the native TYMP and UCK2 fragment peptide chromatographic signature peaks and which can be used as comparator peaks. Thus when the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein digest from the formalin-fixed biological/tumor sample. Quantitative data for fragment peptides are displayed according to the amount of protein analyzed per sample.

In order to develop the SRM/MRM assay for the TYMP and UCK2 fragment peptides additional information beyond simply the peptide sequence is utilized by the mass spectrometer. That additional information allows the mass spectrometer, (e.g., a triple quadrupole mass spectrometer) to perform the correct and focused analysis of the specified TYMP and UCK2 fragment peptides. A triple quadrupole mass spectrometer typically is the most suitable instrument for analyzing a single isolated target peptide within a very complex protein lysate that may consist of hundreds of thousands to millions of individual peptides from all the proteins contained within a cell. The additional information provides the triple quadrupole mass spectrometer with the correct directives to allow analysis of a single isolated target peptide within a very complex protein lysate that may consist of hundreds of thousands to millions of individual peptides from all the proteins contained within a cell. Although SRM/MRM assays can be developed and performed on any type of mass spectrometer, including a MALDI, ion trap, ion trap/quadrupole hybrid, or triple quadrupole, presently the most advantageous instrument platform for SRM/MRM assay is often considered to be a triple quadrupole instrument platform. The additional information about target peptides in general, and in particular about the specified TYMP and UCK2 fragment peptides, may include one or more of the mono isotopic mass of each peptide, its precursor charge state, the precursor m/z value, the m/z transition ions, and the ion type of each transition ion. The peptide sequences of the specified TYMP and UCK2 fragment peptides are shown in Table 1.

TABLE 1

| SEQ ID | Peptide Sequence |
| --- | --- |
| SEQ ID NO: 1 | DGPALSGPQSR |
| SEQ ID NO: 2 | LFVDTDADTR |

To determine an appropriate reference level for TYMP and UCK2 quantitation, tumor samples were obtained from a cohort of patients suffering from cancer, in this case gastric cancer. The tumor samples were formalin-fixed using standard methods and the level of TYMP and UCK2 in the samples was measured using the methods as described above. The tissue samples may also be examined using IHC and FISH using methods that are well known in the art. The patients in the cohort had colorectal cancer and were subsequently treated after surgery with the FOLFOX (5-fluorouracil, leucovorin, and oxaliplatin) regimen. Patient response was measured using methods that are well known in the art, for example by recording the disease-free survival and/or overall survival of the patients at time intervals after treatment. A suitable reference level was determined using statistical methods that are well known in the art, for example by determining the lowest p value of a log rank test. Once a reference level had been determined it was used to identify those patients whose TYMP and UCK2 protein expression levels indicate that they may likely benefit from the combination of the FOLFOX treatment regimen. The skilled artisan will recognize the FOLFOX regimen comprising 5-fluorouracil+leucovorin+oxaliplatin is a common treatment regimen for colorectal cancer patients. Levels of TYMP and UCK2 proteins in patient tumor samples are typically expressed in amol/μg, although other units can be used. The skilled artisan will recognize that a reference level can be expressed as a range around a central value, for example, +/−250, 150, 100, 50 or 25 amol/μg.

Because both nucleic acids and protein can be analyzed from the same Liquid Tissue® biomolecular preparation it is possible to generate additional information about disease diagnosis and drug treatment decisions from the nucleic acids in same sample upon which proteins were analyzed. For example, if the TYMP and UCK2 proteins are expressed by certain cells at increased levels, when assayed by SRM the data can provide information about the state of the cells and their potential for uncontrolled growth, choice of optimal therapy, and potential drug resistance. At the same time, information about the status of genes and/or the nucleic acids and proteins they encode (e.g., mRNA molecules and their expression levels or splice variations) can be obtained from nucleic acids present in the same Liquid Tissue® biomolecular preparation. Nucleic acids can be assessed together or simultaneously to the SRM analysis of proteins, including the TYMP and UCK2 proteins. In one embodiment, information about the TYMP and UCK2 proteins and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

In one embodiment, a method of treating a patient suffering from cancer, especially colon cancer, is provided comprising:
  a) quantifying the level of a specified TYMP fragment peptide and quantifying the level of a specified UCK2 fragment peptide in a protein digest prepared from a tumor tissue sample obtained from the patient and calculating the level of the TYMP and UCK2 peptides in said sample by selected reaction monitoring using mass spectrometry;
  b) comparing the level of said TYMP fragment peptide to a TYMP reference level and comparing the level of said UCK2 fragment peptide to a UCK2 reference level, and
  c) treating the patient with a therapeutic regimen comprising administration of the FOLFIRI regimen (irinotecan/5-fluoruracil/folinic acid) when the level of the TYMP fragment peptide is above said TYMP reference level, and/or the level of the UCK2 fragment peptide is above said UCK2 reference level, or
  d) treating the patient with a therapeutic regimen other than a regimen comprising administration of the FOLFIRI regimen (irinotecan/5-fluoruracil/folinic acid) when the level of the TYMP fragment peptide is below said reference level, and/or the level of the UCK2 fragment peptide is below said reference level.

EXAMPLES

Example 1

Figure 1B:
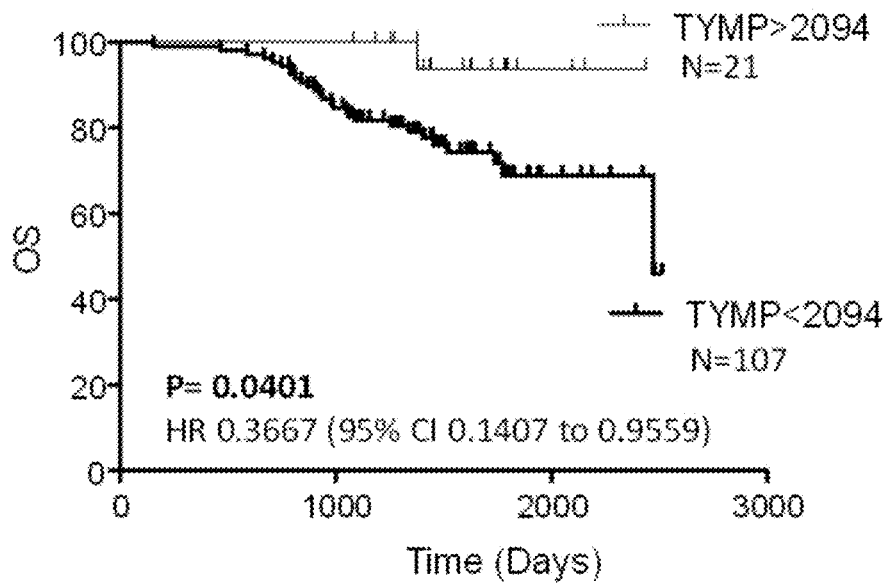

TYMP was assessed by determining the association between its protein levels and Disease-Free Survival (DFS) and Overall Survival (OS) in a univariate Cox model for treatment with the FOLFOX (5-fluorouracil, leucovorin, and oxaliplatin) regimen. Performing data analysis using the continuous TYMP data a cutoff threshold was derived for dichotomizing patients by TYMP levels using Cox proportional modeling. Kaplan Meier curves of the dataset stratified by binary TYMP groups were constructed for visualization. FIGS. 1A and 1B show the Kaplan Meier disease-free survival (DFS) and the overall survival (OS) curves, respectively, using only the TYMP protein levels. A threshold of 2094 amol/ug was selected to test the possibility of patient population separation. As a continuous variable, there is slight separation of the 2 patient populations and an association between TYMP levels and DFS with borderline significance (p=0.0533; HR 0.4653 (95% CI 0.2142 to 1.011). There is statistical significance to a predictive value for treatment outcome using these TYMP expression level parameters with OS (p=0.0401; HR 0.3667 (95% CI 0.1407 to 0.9559). 21 patients show TYMP levels >2094 amol/ug and 107 patients show TYMP levels <2094 amol/ug.

Example 2

Figure 2A:
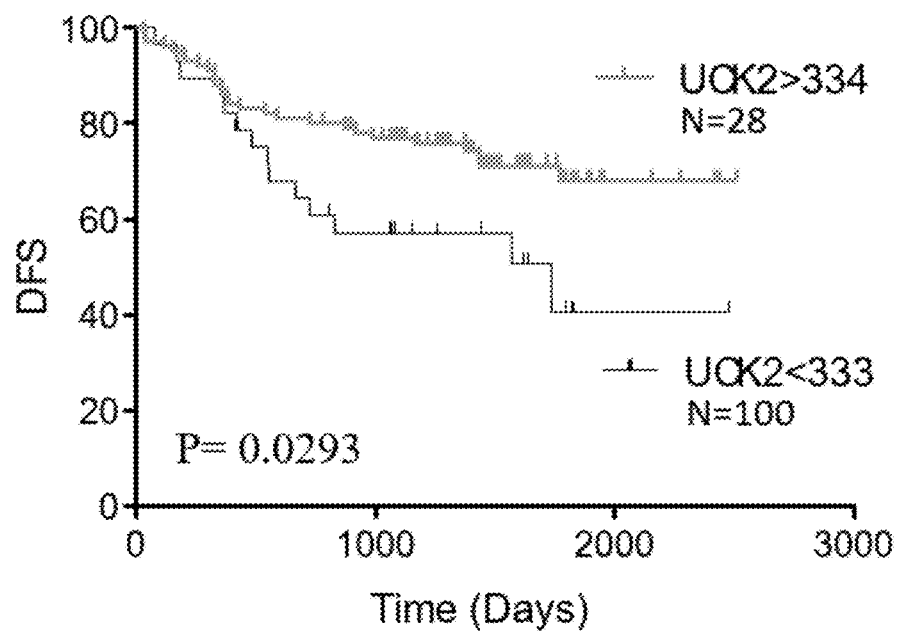
FIGS. 2A and 2B show the Kaplan Meier disease-free survival (DFS) and the overall survival (OS) curves, respectively, using only the UCK2 protein levels. Quantitative levels of UCK2≤333 amol/ug and UCK2≥334 amol/ug cutoff for this colorectal cancer (CRC) cohort treated with the FOLFOX regimen showed predictive value. Results indicate: a) a statistically-significant predictive value for DFS of CRC cancer patients (n=128) based on UCK2 protein levels (Mantel-Cox Test p=0.0293) and b) statistically-significant predictive value for OS of CRC cancer patients (n=128) based on UCK2 protein levels (Mantel-Cox Test p=0.0035).
Figure 2B:
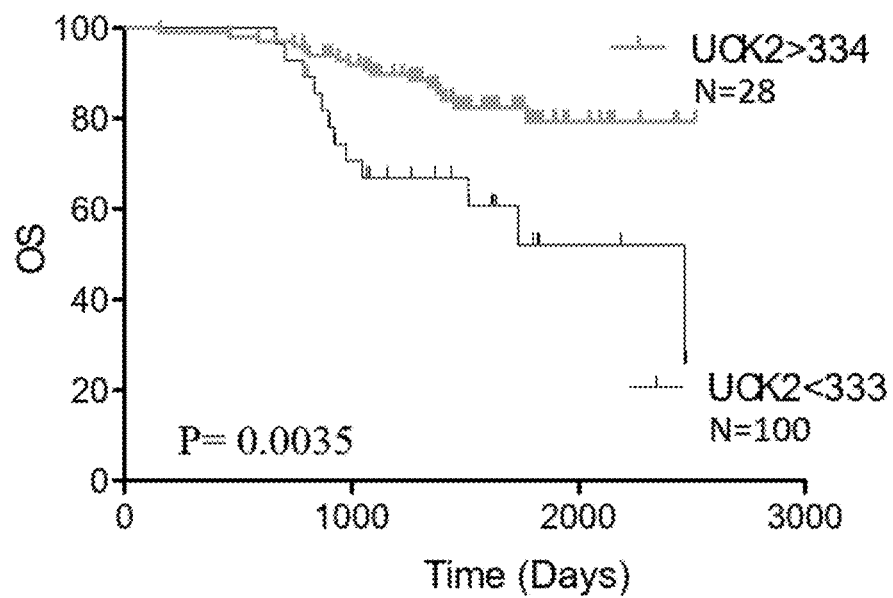

The same analytical approach as described above for TYMP in Example 1 was used to assess associations between UCK2 and DFS/OS in the same patient population treated with FOLFOX. Following the procedure described above, a threshold of 334 amol/ug was selected. FIGS. 2A and 2B show the Kaplan Meier disease-free survival (DFS) and the overall survival (OS) curves, respectively, using only the UCK2 protein levels. As a continuous variable, UCK2 is significantly associated with DFS (Cox test p=0.0293) and is also very significantly associated with OS (Cox test p=0.0035) thus providing predictive value for FOLFOX treatment outcome. 28 patients have UCK2 levels >334 amol/ug and 100 patients have UCK2 levels <333 amol/ug. Kaplan Meier OS curves of the patient cohort using UCK2 levels above and below 334 amol/ug is shown in FIG. 2B.

Example 3

Figure 3A:
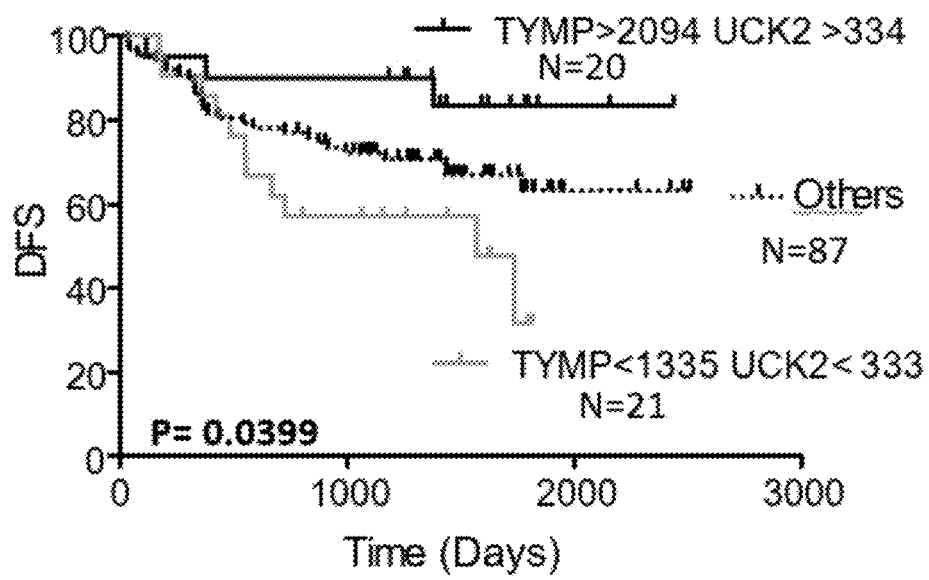
FIGS. 3A and 3B show the Kaplan Meier disease-free survival (DFS) and the overall survival (OS) curves, respectively, using a combination of TYMP protein levels and UCK2 protein levels. Results indicate: a) a statistically-significant predictive value for DFS of CRC cancer patients (n=128) based on combining UCK2≤333 amol/ug and TYMP≤1335 amol/ug protein levels when compared to combining UCK2≥334 amol/ug and TYMP≥2095 amol/ug protein levels (Mantel-Cox Test p=0.0399), b) a statistically-significant predictive value for OS of CRC cancer patients (n=128) based on combining UCK2≤333 amol/ug and TYMP≤1335 amol/ug protein levels when compared to combining UCK2≥334 amol/ug and TYMP≥2095 amol/ug protein levels (Mantel-Cox Test p=0.0101), and c) patients whose tissue samples not showing either of these 2 protein expression profiles (TYMP≤1335/UCK2≤333: TYMP≥2095/UCK2≥334) have intermediate predictive results indicating that definitive therapeutic outcome prediction cannot be determined for these patients.
Figure 3B:
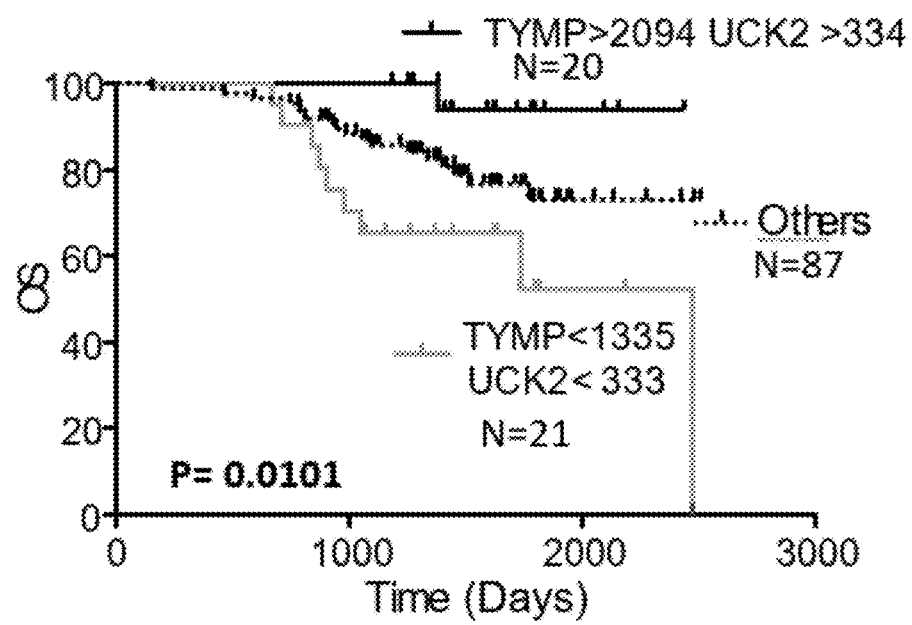

FIGS. 3A and 3B show the Kaplan Meier disease-free survival (DFS) and the overall survival (OS) curves, respectively, using a combination of TYMP protein levels and UCK2 protein levels. The Kaplan Meier DFS/OS curves stratified this patient cohort into 3 distinct TYMP/UCK2 groups. When the patient cohort was analyzed using TYMP expression levels at 2 significantly different selected thresholds (TYMP<1335 amol/ug; TYMP>2094 amol/ug) combined with the previously-defined single UCK2 expression level (UCK2<333 amol/ug; UCK2>334 amol/ug), Kaplan Meier OS curves stratified 2 distinct patient populations that define statistically significant different therapeutic outcomes for both DFS and OS to treatment of colon cancer patients with FOLFOX. There are 20 patients whose tumor cells express the combination of TYMP>2094 amol/ug and UCK2>334 amol/ug and this patient group shows dramatically successful response to FOLFOX treatment post-surgery with high statistical significance (Cox test p=0.00399 for DFS and p=0.0101 for OS). There are 21 patients whose tumor cells express the combination of TYMP>1335 amol/ug and UCK2<333 amol/ug and this patient group shows little to no response to FOLFOX treatment post-surgery with statistical significance (Cox test p=0.00399 for DFS and p=0.0101). There is third patient group defined by these TMP/UCK2 expression levels that is indeterminate in terms of treatment success with FOLFOX. There are 87 patients that show intermediate success whereby more patients in this group show higher DFS and OS than the lower group of 21 patients yet show lower DFS and OS than the higher survival group of 20 patients.

What is claimed is:

1. A method of treating a patient suffering from colon cancer, the method comprising: administering a therapeutic regimen comprising irinotecan, 5-fluoruracil, and folinic acid to the patient,
   wherein the patient exhibits a TYMP fragment peptide level above 1135 amol/µg protein and a UCK2 fragment peptide level above 333 amol/µg protein in a protein-digested, formalin-fixed tumor sample when analyzed by mass spectrometry;
   wherein the TYMP fragment peptide is the peptide according to SEQ ID NO:1; and
   wherein the UCK2 fragment peptide is the peptide according to SEQ ID NO:2.

2. The method of claim 1, further comprising heating a composition comprising the formalin-fixed tumor sample and a reaction buffer at a temperature from 80° C. to 100° C. for a period of time from 10 minutes to 4 hours.

3. The method of claim 2, wherein the protein-digested, formalin-fixed tumor sample was treated with an effective amount of a proteolytic enzyme selected from the group consisting of trypsin, chymotrypsin, and endoproteinase Lys-C for a period of time from 30 minutes to 24 hours at a temperature from 37° C. to 65° C.

4. The method of claim 3, wherein the proteolytic enzyme is trypsin.

5. The method of claim 1, wherein the mass spectrometry comprises tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry.

6. The method of claim 5, wherein a mode of the mass spectrometry used is Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

7. The method of claim 1, wherein the formalin-fixed tumor sample is a cell, collection of cells, or a solid tissue.

8. The method of claim 7, wherein the protein-digested, formalin-fixed tumor sample is formalin fixed solid tissue.

9. The method of claim 8, wherein the tissue is paraffin embedded tissue.

10. The method of claim 1, wherein the TYMP fragment peptide level is determined by comparing the amount of the TYMP peptide in the sample to a spiked internal standard peptide of known amount, wherein both the native peptide in the sample and the internal standard peptide corresponds to the same amino acid sequence of the TYMP fragment peptide of SEQ ID NO:1.

11. The method of claim 10, wherein the internal standard peptide is an isotopically labeled peptide.

12. The method of claim 10, wherein the isotopically labeled internal standard peptide comprises one or more heavy stable isotopes selected from the group consisting of $^{18}O$, $^{17}O$, $^{15}N$, $^{13}C$, $^{2}H$, and a combination thereof.

13. The method of claim 1, wherein the UCK2 fragment peptide level is determined by comparing the amount of the UCK2 peptide in the sample to a spiked internal standard peptide of known amount, wherein both the native peptide in the sample and the internal standard peptide corresponds to the same amino acid sequence of the UCK2 fragment peptide of SEQ ID NO:2.

14. The method of claim 13, wherein the internal standard peptide is an isotopically labeled peptide.

15. The method of claim 13, wherein the isotopically labeled internal standard peptide comprises one or more heavy stable isotopes selected from the group consisting of $^{18}O$, $^{17}O$, $^{15}N$, $^{13}C$, $^{2}H$ and a combination thereof.

16. The method of claim 10, wherein quantifying the UCK2 fragment peptide comprises determining the amount of the UCK2 peptide in the sample by comparing to a spiked internal standard peptide of known amount, wherein both the native peptide in the sample and the internal standard peptide corresponds to the same amino acid sequence of the UCK2 fragment peptide as shown in SEQ ID NO:2.

17. The method of claim 11, wherein quantifying the UCK2 fragment peptide comprises determining the amount of the UCK2 peptide in the sample by comparing to a spiked internal standard peptide of known amount, wherein both the native peptide in the sample and the internal standard peptide corresponds to the same amino acid sequence of the UCK2 fragment peptide as shown in SEQ ID NO:2.

18. The method of claim 12, wherein quantifying the UCK2 fragment peptide comprises determining the amount of the UCK2 peptide in the sample by comparing to a spiked internal standard peptide of known amount, wherein both the native peptide in the sample and the internal standard peptide corresponds to the same amino acid sequence of the UCK2 fragment peptide as shown in SEQ ID NO:2.

19. The method of claim 18, wherein the internal standard peptide is an isotopically labeled peptide.

20. The method of claim 19, wherein the isotopically labeled internal standard peptide comprises one or more heavy stable isotopes selected from the group consisting of $^{18}O$, $^{17}O$, $^{15}N$, $^{13}C$, $^{2}H$, and a combination thereof.

* * * * *

SEQUENCE LISTING

<160> NUMBER OF SEQ ID NOS: 2

<210> SEQ ID NO 1
<211> LENGTH: 11
<212> TYPE: PRT
<213> ORGANISM: Homo sapiens

<400> SEQUENCE: 1

Asp Gly Pro Ala Leu Ser Gly Pro Gln Ser Arg
1               5                   10

<210> SEQ ID NO 2
<211> LENGTH: 10
<212> TYPE: PRT
<213> ORGANISM: Homo sapiens

<400> SEQUENCE: 2

Leu Phe Val Asp Thr Asp Ala Asp Thr Arg
1               5                   10